United States Patent [19]
Cozean, Jr. et al.

[11] Patent Number: 5,269,787
[45] Date of Patent: Dec. 14, 1993

[54] APPARATUS AND METHOD FOR CAPSULORHEXIS

[76] Inventors: Charles H. Cozean, Jr., Rte. 2, Box 383D, Cape Girardeau, Mo. 63701; Charles Cozean, III, 11930 Montana Ave., Apt. 304, Los Angeles, Calif. 90049

[21] Appl. No.: 808,650

[22] Filed: Dec. 17, 1991

[51] Int. Cl.⁵ ............................................. A61F 9/00
[52] U.S. Cl. ................................. 606/107; 606/166; 606/167; 606/169; 606/170; 606/171; 604/22
[58] Field of Search ........................... 606/79-81, 606/107, 161, 166, 167, 169-171, 180; 604/22; 30/301, 316, 45

[56] References Cited

U.S. PATENT DOCUMENTS

| | | | |
|---|---|---|---|
| 2,473,968 | 6/1949 | Paton | 606/166 |
| 4,020,847 | 5/1977 | Clark | 606/180 |
| 4,188,952 | 2/1980 | Loschilov et al. | 606/170 |
| 4,345,516 | 8/1982 | Sinclair | 30/316 |
| 4,406,285 | 9/1983 | Villasenor et al. | 606/166 |
| 4,425,115 | 1/1984 | Wuchinich | |
| 4,515,583 | 5/1985 | Sorich | |
| 4,672,965 | 6/1987 | Baum | |
| 4,739,761 | 4/1988 | Grandon | 606/166 |
| 4,766,897 | 8/1988 | Smirmaul | 606/107 |
| 4,844,060 | 7/1989 | Krumeich | 606/166 |
| 4,846,833 | 7/1989 | Cumming | |
| 4,878,912 | 11/1989 | Castleman | |
| 4,911,161 | 3/1990 | Schechter | 606/107 |
| 5,030,201 | 7/1991 | Palestrant | 604/22 |
| 5,108,412 | 4/1992 | Krumeich et al. | 606/107 |

FOREIGN PATENT DOCUMENTS

| | | | |
|---|---|---|---|
| 0591498 | 1/1934 | Fed. Rep. of Germany | 606/161 |
| 2811869 | 9/1979 | Fed. Rep. of Germany | 606/166 |
| 0242673 | 2/1987 | Fed. Rep. of Germany | 606/166 |
| 2588751 | 4/1987 | France | 606/166 |
| 0448013 | 10/1974 | U.S.S.R. | 606/166 |
| 1335282 | 9/1987 | U.S.S.R. | 606/166 |
| 1431752 | 10/1988 | U.S.S.R. | 606/107 |
| 1500292 | 8/1989 | U.S.S.R. | 606/107 |
| 1526704 | 12/1989 | U.S.S.R. | 606/110 |
| 1535541 | 1/1990 | U.S.S.R. | 606/166 |

OTHER PUBLICATIONS

"Intraocular tissues are different. Shouldn't your cutters be? SITE TXR cutters are," Ophthalmology Times, Jul. 15, 1984, p. 61.

Journal of Ocular Therapy & Surgery, the Journal for Practicing Ophthalmologists, vol. 3, No. 1 Jan-Feb 1984, pages unknown.

"Anterior capsultomy with ultrasound cystotme" by A. Mendez, M.D., American Intraocular Implant Society Journal, vol. 10, Summer 1984, pp. 363-364.

"Visitec offers a cystotome to fit your capsulotomy technique" Booth No. 215 AIOIS meeting (date and other information unknown).

"Battery-Powered Unit Aids Anterior Capsulectomy" IOL & Ocular Surgery News, Jul. 15, 1984, pp.23.

Primary Examiner—Stephen C. Pellegrino
Assistant Examiner—Glenn Dawson
Attorney, Agent, or Firm—Herbert J. Hammond

[57] ABSTRACT

Surgical apparatus and method for incising an aperture in the anterior capsule of the human eye. The apparatus for capsulorhexis comprises a shaft, a cutting member with a sharp cutting edge, and a fastener connecting the shaft to an ultrasonic power source. After making an initial incision in the eye, the surgeon uses the apparatus to make a smooth, continuous, curvilinear aperture in the anterior capsule of the eye.

13 Claims, 3 Drawing Sheets

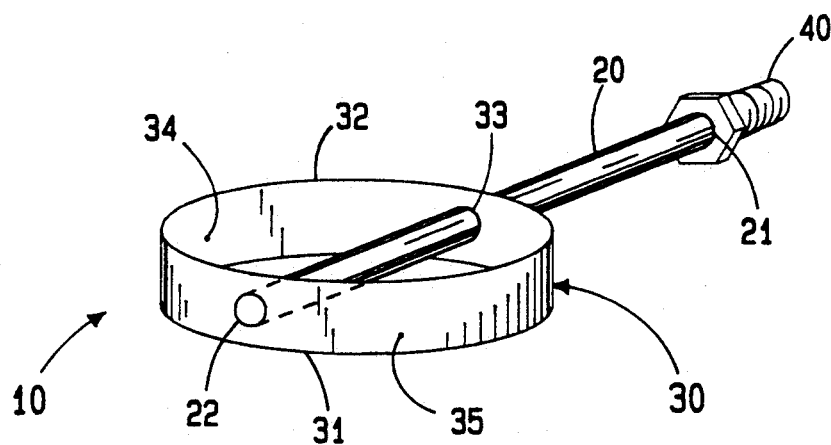
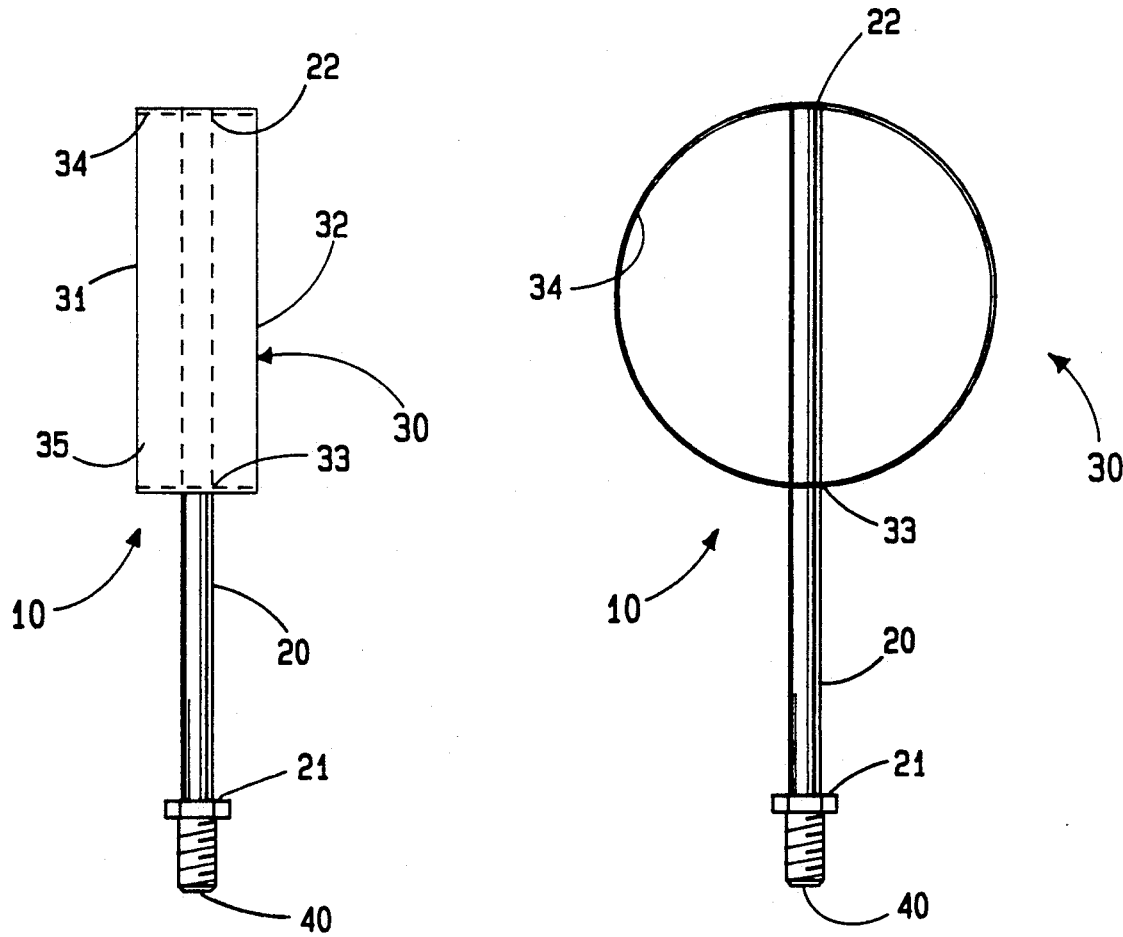
FIG.1
FIG.2
FIG.3

APPARATUS AND METHOD FOR CAPSULORHEXIS

TECHNICAL FIELD

This invention relates to surgical instruments, and more particularly to surgical instruments associated with intraocular lens implantation.

BACKGROUND OF THE INVENTION

Development of cataracts, a clouding of the material within the lens capsule of the eye, is a common accompaniment to the aging process. In response to this routine problem, eye surgeons have developed several techniques for cataract extraction. Generally, cataract extraction involves making an incision through the anterior surface of the lens capsule. Clouded material is removed through suction of the lens nucleus emulsion (phacoemulsification), without removing the entire lens capsule. After surgery, since a portion of the natural lens of the eye has been removed, light entering the eye through the cornea and pupil is unfocused. Therefore, an artificial intraocular lens is usually implanted directly into the eye after cataract extraction.

An essential step in cataract extraction is the incision of the anterior lens capsule. Current technique, called capsulotomy, uses a straight intravenous needle with a sharp wedge attached to one end. The wedge is used manually or driven ultrasonically in a chopping motion to perforate the anterior capsule. This technique produces a hole with jagged edges, similar to the edges produced when one opens a can with a manual can opener.

Although this technique has been widely used in conjunction with cataract extractions, it is not entirely satisfactory. The incision resulting from a capsulotomy is of an unpredictable geometry and is susceptible to linear tears. In the worst case, such tears in the capsule can result in the release of the lens nucleus into the vitreous cavity of the eye. In addition, capsulotomy produces an irregular aperture in the anterior capsule, which leads to asymmetrical scarring. This condition may allow the implanted intraocular lens to migrate out of the visual axis subsequent to surgery. Moreover, capsulotomy produces a large aperture which allows nuclear lens debris from phacoemulsification to impact the corneal endothelium. Normally, the corneal endothelium keeps the cornea optimally hydrated. Injury to this layer by impacted nuclear debris from phacoemulsification may lead to corneal edema and ultimately an irreversible clouding of the cornea.

SUMMARY OF THE INVENTION

The present invention comprises a novel surgical apparatus and method which overcomes the foregoing disadvantages associated with the prior art. The apparatus for capsulorhexis includes a shaft, a cutting member with a sharp cutting edge, and a fastener which connects the shaft to an ultrasonic power source. The cutting member works in conjunction with the ultrasonic power source to produce a smooth, continuous aperture in the anterior capsule of the eye. The aperture is smaller and of a more controlled geometry than that produced by current techniques. This smaller aperture prevents nuclear lens debris from impacting the corneal endothelium and significantly reduces the likelihood of corneal edema and subsequent clouding.

Another advantage of the present invention is that the single cut produced by the apparatus for capsulorhexis promotes symmetrical scarring and implant fixation in the visual axis.

The apparatus and method for capsulorhexis of the present invention may be used to produce a small aperture in the anterior capsule. Other advantages and applications deriving from the use of the invention will readily suggest themselves to those skilled in the art.

DESCRIPTION OF THE DRAWINGS

A more complete understanding of the invention and the advantages thereof may be had by reference to the following Detailed Description when taken in conjunction with the accompanying Drawings wherein:

FIG. 1 is a perspective view of the preferred embodiment of the invention illustrating various features of the invention;

FIG. 2 is a side view of the preferred embodiment of the invention illustrating the two surfaces of the cutting member;

FIG. 3 is a top view of the preferred embodiment of the invention illustrating the relationship between the shaft and the cutting member;

DETAILED DESCRIPTION OF THE INVENTION

Figure 4:
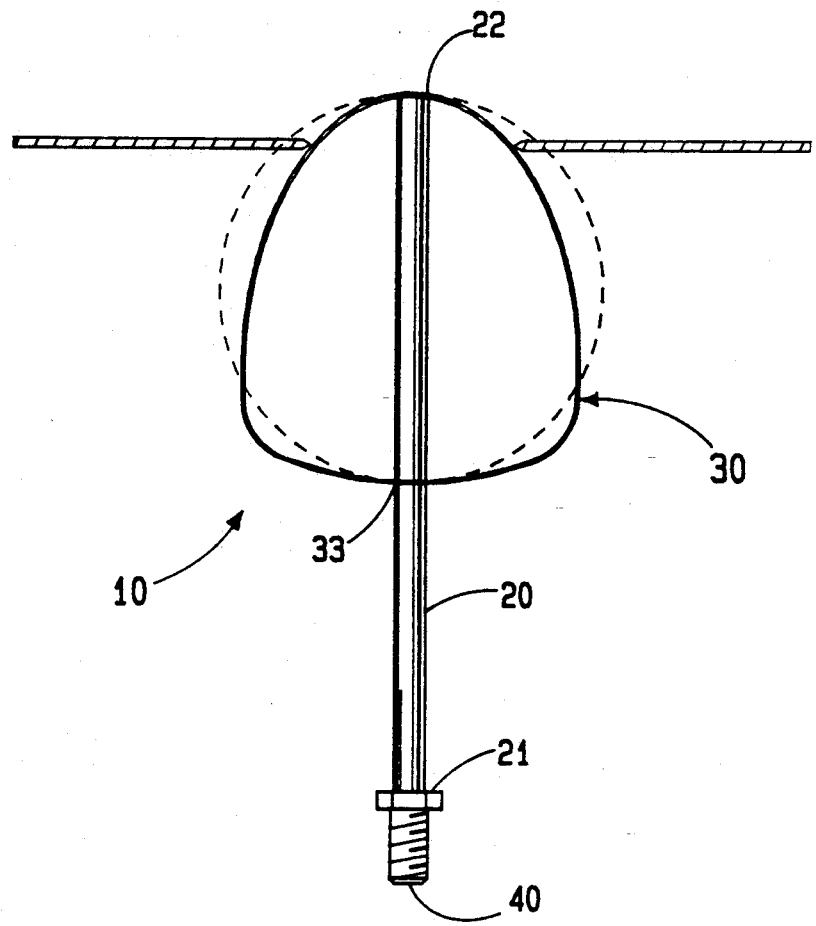
FIG. 4 is a top view of the preferred embodiment of the invention showing the deformation of the instrument as it enters the incision.

Referring now to the Drawings and in particular to FIG. 1, there is shown an apparatus for capsulorhexis 10 for incising a small circular aperture in the anterior capsule of the eye. The apparatus for capsulorhexis 10 includes a shaft 20, a cutting member 30 having at least one sharp cutting edge 31, and a fastener 40 which connects the shaft 20 to an ultrasonic power source.

The shaft 20 has a first end 21 and a second end 22. The first end 21 of the shaft 20 terminates in a threaded fastener 40. The fastener 40 connects to an ultrasonic power source (not shown).

The cutting member 30 is composed of a hardened but flexible metal alloy. A titanium aluminum/vanadium alloy or stainless steel alloy is desirable, however, other flexible metal alloys known in the art may also be used. The cutting member 30 has an interior surface 34 and an exterior surface 35, and two edges: the sharp cutting edge 31 and the blunt edge 32.

The cutting member 30 attaches to the shaft 20 at two points. The second end 22 of the shaft 20 terminates at a point on the interior surface 34 of the cutting member 30. In addition, the cutting member 30 includes an opening 33 equal in diameter to the diameter of the shaft 20, through which the shaft 20 protrudes.

After the surgeon makes the initial incision in the eye, the cutting member 30 works in conjunction with the ultrasonic power source to perforate the anterior capsule within the eye. Following this perforation, the cataract may be extracted. When used with the power source, the cutting edge 31 moves with a vibratory motion. This technique, wherein the cutting member 30 acts like a cookie cutter, is called capsulorhexis.

The cutting edge 31 produces a smooth, continuous, curvilinear aperture of predetermined geometry in the anterior capsule. The aperture is approximately 50% smaller than that produced by a capsulotomy. In addition, the aperture produced by the apparatus for capsulorhexis 10 has a more controlled geometry than that produced by prior art surgical instruments.

The single cut and resultant small aperture produced by the apparatus for capsulorhexis 10 prevents debris from being deposited on the cornea during cataract extraction, and decreases the likelihood that a subsequently implanted lens will migrate.

Turning to FIG. 2, therein is shown a side view of the preferred embodiment of the invention. The first end 21 of the shaft 20 is attached to the fastener 40 which connects to the ultrasonic power source. The cutting member 30 attaches to the shaft 20 at the second end 22 and opening 33. The cutting member 30 has a sharp cutting edge 31 and a blunt edge 32, and an interior surface 34 and an exterior surface 35.

Turning to FIG. 3, therein is shown a top view of the preferred embodiment of the invention. The second end 22 of the shaft 20 terminates at a point on the interior surface 34 of the cutting member 30. In addition, the shaft 20 protrudes through an opening 33 in the cutting member 30.

Referring now to FIG. 4, therein is shown the deformation of the cutting member 30 as it enters the incision in the eye. FIG. 4 is an enlarged view of the apparatus for capsulorhexis 10 entering the eye. The metal alloy of which the cutting member 30 is composed is sufficiently flexible to permit the illustrated deformation. Although the cutting member 30 deforms through the incision, it returns to its original circular form once admitted through the incision.

Figure 5:
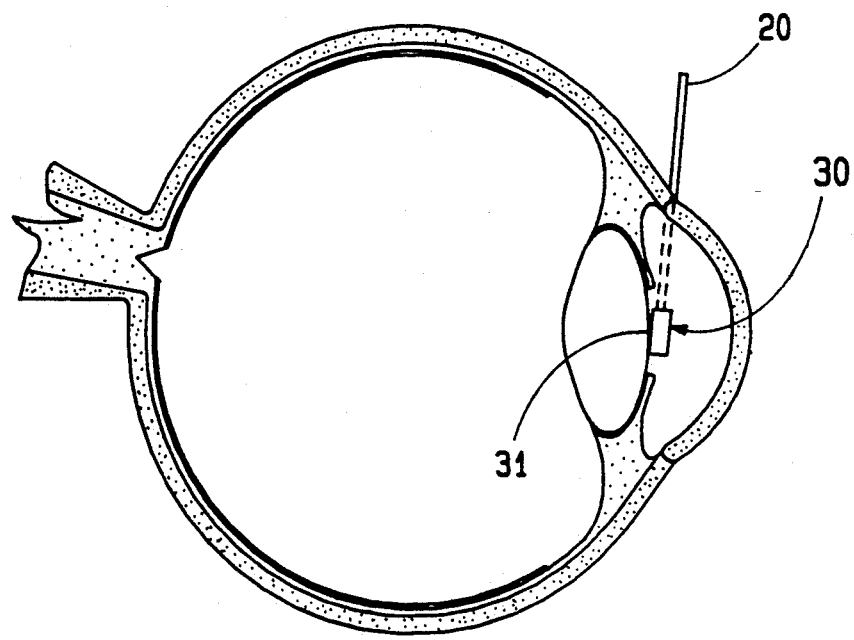
FIG. 5 is a cross-sectional side view of the eye illustrating the position of the apparatus relative to the eye during the initial stage of the capsulorhexis procedure.

Turning to FIG. 5, therein is shown the apparatus for capsulorhexis 10 positioned at the surface of the anterior capsule, after introduction of the apparatus for capsule 10 through an incision made in the eye using instruments known in the art. Although the cutting member 30 deforms as it enters the incision, it returns to its original form once admitted through the incision.

The cutting member 30 is then repositioned inside the eye so that the cutting edge 31 of the cutting member 30 contacts the anterior capsule. The cutting edge 31 is substantially parallel to the plane of the eye.

When the ultrasonic power source is turned on, the cutting edge 31 moves with a vibratory motion so that it perforates the anterior capsule. The sharp cutting edge 31 of the cutting member 30 makes a smooth, continuous, resilient incision in the capsule. When a complete aperture has been accomplished, the cataract may be removed.

In the preferred embodiment of the invention, the direction of vibration of the cutting edge 31 of the cutting member 30 is parallel to the plane of the eye. In the alternative, the direction of ultrasonic translation may be normal to the eye or rotational about an axis normal to the plane of the lens.

Figure 6:
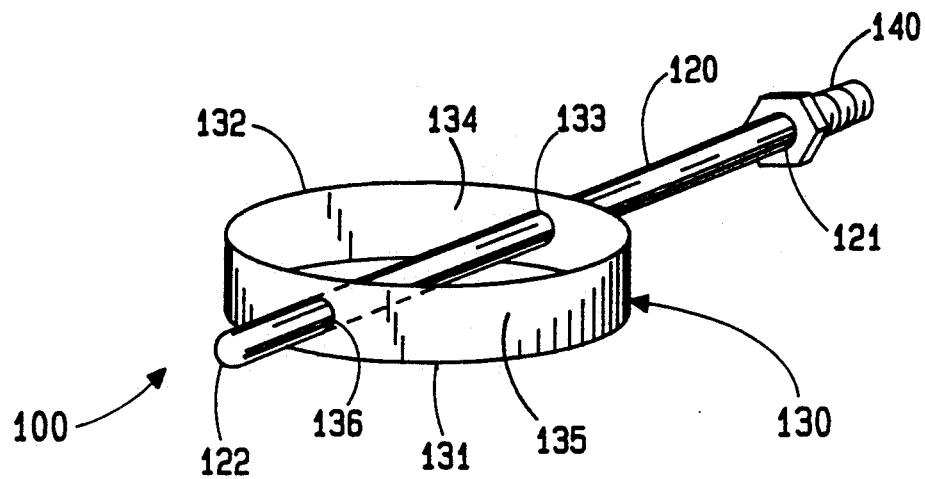
FIG. 6 is a perspective view of an alternate embodiment of the invention showing the shaft extending beyond the cutting member.

Turning to FIG. 6, therein is shown a second embodiment of the apparatus for capsulorhexis 100. A shaft 120 of the apparatus for capsulorhexis 100 has a first end 121 and a second end 122. The shaft 120 connects to a fastener 140 which attaches to an ultrasonic power source.

A cutting member 130 attaches to the shaft 120 at two points. The shaft 120 protrudes through an opening 133 in the cutting member 130, and protrudes through a similar opening 136 on the opposite side of the cutting member 130. The second end 122 of the shaft 120 extends beyond this opening 136. The extension of the second end 122 of the shaft 120 beyond the cutting member 130 provides added strength to the cutting member during cataract extraction.

Figure 7:
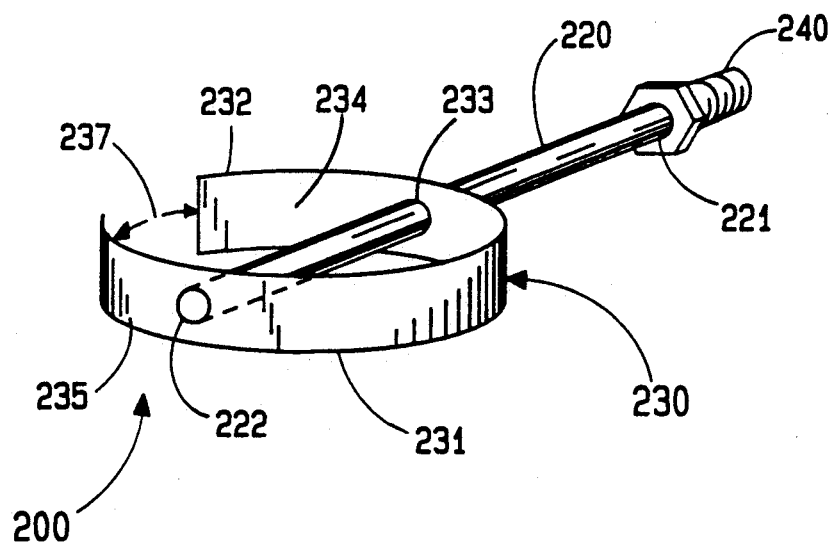
FIG. 7 is a perspective view of an alternate embodiment of the invention illustrating a C-shaped cutting member.

Referring to FIG. 7, therein is shown a third embodiment of the apparatus for capsulorhexis 200. The shaft 220 of the apparatus for capsulorhexis 200 has a first end 221 and a second end 222. The shaft 220 connects to a fastener 240 which attaches to an ultrasonic power source.

The cutting member 230 has a sharp cutting edge 231 and a blunt edge 232, and attaches to the shaft 220 at two points. An opening 233 in the cutting member 230 enables the shaft 220 to protrude through the cutting member 230. In FIG. 7, the second end 222 of the shaft 220 terminates into the cutting member 230. In the alternative, the second end 222 of the shaft 220 may extend beyond the point of attachment of the shaft 220 to the cutting member 230.

The cutting member 230 is shaped like a "C", rather than a circle. There is a gap 237 between the ends of the cutting member 230.

Although preferred and alternate embodiments of the present invention have been illustrated in the accompanying Drawings and described in the foregoing Detailed Description, it will be appreciated by those skilled in the art that various modifications and rearrangements of the component parts and elements of the present invention are possible within the scope of the present invention.

We claim:

1. Apparatus for incising an aperture in the anterior capsule of the human eye comprising:

a solid shaft having first and second ends;

a cutting member attached to the shaft, said cutting member having first, second and third orthogonal axes wherein the first and second axes define a horizontal plane of said cutting member and the third axis defines the depth of said cutting member, said cutting member comprising a metal band having a physical configuration defined by the first and second axes, with the width of said band substantially equal to the length of said third axis, said metal band having at least one opening therein receiving said shaft therethrough and having a cutting edge; and means for connecting the first end of said shaft to an ultrasonic power source to impart motion to the cutting edge.

2. Apparatus as set forth in claim 1 wherein the cutting member is composed of a hardened metal alloy.

3. Apparatus as set forth in claim 2 wherein the metal alloy is a titanium aluminum/vanadium alloy.

4. Apparatus as set forth in claim 2 wherein the metal alloy is a stainless steel alloy.

5. Apparatus as set forth in claim 1 wherein the cutting member is circular.

6. Apparatus as set forth in claim 1 wherein the second end of the shaft terminates at the cutting member.

7. Apparatus as set forth in claim 1 wherein metal band has a second opening therein receiving the second end of the shaft therethrough.

8. Apparatus as set forth in claim 1 wherein the cutting member is shaped like a "C".

9. Apparatus as set forth in claim 1 wherein the means for connecting the shaft to the ultrasonic power source comprises a fastener.

10. Apparatus for incising an aperture in the anterior capsule of the human eye comprising:
- a deformable, circular cutting member of a metal alloy, said member having a cutting edge and at least one opening therein;
- a solid shaft having first and second ends wherein the second end of the shaft is inserted through the opening in and terminates against said cutting member; and
- a fastener on the first end of said shaft adapted to connect said first end of said shaft to an ultrasonic power source to impart motion to the cutting edge.

11. Apparatus for incising an aperture in the anterior capsule of the human eye comprising:
- a deformable, circular cutting member of a metal alloy, said member having a cutting edge and at least two openings therein;
- a solid shaft having first and second ends said shaft attached to said circular cutting member such that said shaft passes through the openings in said cutting member; and
- a fastener on the first end of said shaft adapted to connect said first end of said shaft to an ultrasonic power source to impart motion to the cutting edge.

12. Apparatus for incising an aperture in the anterior capsule of the human eye comprising:
- a "C"-shaped cutting member of a metal alloy, said member having a cutting edge and at least one opening therein;
- a solid shaft having first and second ends, said shaft attached to said c-shaped cutting member such that wherein the second end of the shaft passes through the opening in said cutting member; and
- a fastener on the first end of said shaft adapted to connect said first end of said shaft to an ultrasonic power source to impart motion to the cutting edge.

13. Apparatus for incising an aperture in the anterior capsule of the human eye comprising:
- a "C"-shaped cutting member of a metal alloy, said member having a cutting edge and at least two openings therein;
- a solid shaft having first and second ends, said shaft attached to said c-shaped cutting member such that wherein the shaft passes through the openings in said cutting member; and
- a fastener on the first end of said shaft adapted to connect said first end of said shaft to an ultrasonic power source to impart motion to the cutting edge.

* * * * *

UNITED STATES PATENT AND TRADEMARK OFFICE
CERTIFICATE OF CORRECTION

PATENT NO. : 5,269,787
DATED : December 14, 1993
INVENTOR(S) : Charles H. Cozean, Jr., et al.

It is certified that error appears in the above-identified patent and that said Letters Patent is hereby corrected as shown below:

On title page, item [76] between "Charles" and "Cozean, III"
insert the initial --H.--;

Signed and Sealed this

Eighth Day of November, 1994

Attest:

BRUCE LEHMAN

*Attesting Officer*     *Commissioner of Patents and Trademarks*